United States Patent
Milliman et al.

(10) Patent No.: US 8,453,911 B2
(45) Date of Patent: Jun. 4, 2013

(54) SURGICAL STAPLER

(75) Inventors: Keith L. Milliman, Bethel, CT (US);
Ryan Williams, Southbury, CT (US);
Nihir Patel, Stamford, CT (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 13/589,100

(22) Filed: Aug. 18, 2012

(65) Prior Publication Data

US 2012/0305625 A1 Dec. 6, 2012

Related U.S. Application Data

(63) Continuation of application No. 12/819,408, filed on Jun. 21, 2010, now Pat. No. 8,267,301.

(60) Provisional application No. 61/235,131, filed on Aug. 19, 2009.

(51) Int. Cl.
*A61B 17/068* (2006.01)

(52) U.S. Cl.
USPC ....... 227/176.1; 227/19; 227/180.1; 606/139; 606/219

(58) Field of Classification Search
USPC .................. 227/19, 175.1, 175.2, 180.1, 119, 227/176.1; 606/139, 219
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev | |
| 3,606,888 A * | 9/1971 | Willkinson | 227/179.1 |
| 3,638,652 A | 2/1972 | Kelley | |
| 3,771,526 A | 11/1973 | Rudie | |
| 4,198,982 A * | 4/1980 | Fortner et al. | 227/179.1 |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,354,628 A * | 10/1982 | Green | 227/19 |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |

(Continued)

FOREIGN PATENT DOCUMENTS

| | | |
|---|---|---|
| CA | 908529 | 8/1972 |
| DE | 3301713 | 11/1989 |

(Continued)

*Primary Examiner* — Scott A. Smith (57) ABSTRACT

A surgical stapler includes a handle assembly, an elongated body portion extending distally from the handle assembly, and a head portion disposed adjacent a distal portion of the elongated body portion and including an anvil assembly and a shell assembly. The anvil assembly is movable in relation to the shell assembly between spaced and approximated positions. The shell assembly includes a pusher movable distally to advance staples from the shell assembly into contact with the anvil assembly. First and second alignment pins operatively associated with the pusher have distal ends positioned distally of the pusher, the alignment pins movable between a first non-engaged position spaced from the anvil assembly and a second position in engagement with the anvil assembly.

18 Claims, 7 Drawing Sheets

U.S. PATENT DOCUMENTS

| | | | |
|---|---|---|---|
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,610,383 A * | 9/1986 | Rothfuss et al. | 227/19 |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,071,052 A * | 12/1991 | Rodak et al. | 227/175.2 |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,413,267 A | 5/1995 | Solyntjes et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A * | 11/1995 | Rodak | 227/176.1 |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,794,834 A | 8/1998 | Hamblin et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,964,394 A * | 10/1999 | Robertson | 227/176.1 |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |

| Patent No. | Date | Inventor |
|---|---|---|
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 * | 4/2004 | Whitman .................. 606/219 |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,817,508 B1 * | 11/2004 | Racenet et al. ............ 227/176.1 |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 * | 12/2005 | Bilotti et al. ............... 227/180.1 |
| 6,981,941 B2 | 1/2006 | Whitman et al. |
| 6,988,650 B2 * | 1/2006 | Schwemberger et al. . 227/176.1 |
| 7,032,798 B2 | 4/2006 | Whitman et al. |
| 7,059,331 B2 | 6/2006 | Adams et al. |
| 7,059,510 B2 | 6/2006 | Orban, III |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,303,106 B2 * | 12/2007 | Milliman et al. ......... 227/175.1 |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 * | 7/2009 | Milliman ................... 227/182.1 |
| 7,559,451 B2 | 7/2009 | Sharma et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,717,312 B2 * | 5/2010 | Beetel ........................ 227/175.1 |
| 7,766,207 B2 * | 8/2010 | Mather et al. .............. 227/175.1 |
| 7,909,223 B2 | 3/2011 | Cole et al. |
| 8,002,795 B2 * | 8/2011 | Beetel ............................ 606/219 |
| 8,267,301 B2 * | 9/2012 | Milliman et al. .......... 227/176.1 |
| 2001/0000903 A1 | 5/2001 | Heck et al. |
| 2001/0010320 A1 | 8/2001 | Bolduc et al. |
| 2001/0054636 A1 | 12/2001 | Nicolo |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0144675 A1 | 7/2003 | Nicolo |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2005/0006433 A1 | 1/2005 | Milliman et al. |
| 2005/0021053 A1 | 1/2005 | Heinrich |
| 2005/0023325 A1 | 2/2005 | Gresham et al. |
| 2005/0051597 A1 | 3/2005 | Toledano |
| 2005/0067454 A1 | 3/2005 | Vresh et al. |
| 2005/0087580 A1 | 4/2005 | Orban, III |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2005/0205639 A1 | 9/2005 | Milliman et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0047308 A1 | 3/2006 | Ortiz et al. |
| 2006/0049231 A1 | 3/2006 | Leiboff et al. |
| 2006/0085032 A1 | 4/2006 | Viola |
| 2006/0085033 A1 | 4/2006 | Criscuolo et al. |
| 2006/0085034 A1 | 4/2006 | Bettuchi |

| | | |
|---|---|---|
| 2006/0085035 A1 | 4/2006 | Viola |
| 2006/0097025 A1 | 5/2006 | Milliman et al. |
| 2006/0108393 A1 | 5/2006 | Heinrich et al. |
| 2006/0144897 A1 | 7/2006 | Jankowski et al. |
| 2006/0151567 A1 | 7/2006 | Roy |
| 2006/0191975 A1 | 8/2006 | Adams et al. |
| 2006/0201989 A1 | 9/2006 | Ojeda |
| 2006/0201993 A1 | 9/2006 | Hur |
| 2006/0241692 A1 | 10/2006 | McGuckin, Jr. et al. |
| 2006/0255090 A1 | 11/2006 | Milliman et al. |
| 2006/0289601 A1 | 12/2006 | Orban, III |
| 2007/0023475 A1 | 2/2007 | Csiky |
| 2007/0027473 A1 | 2/2007 | Vresh et al. |
| 2007/0029363 A1 | 2/2007 | Popov |
| 2007/0034666 A1 | 2/2007 | Holsten et al. |
| 2007/0034667 A1 | 2/2007 | Holsten et al. |
| 2007/0034668 A1 | 2/2007 | Holsten et al. |
| 2007/0038248 A1 | 2/2007 | Heinrch |
| 2007/0060952 A1 | 3/2007 | Roby et al. |
| 2007/0181632 A1 | 8/2007 | Milliman et al. |
| 2008/0054045 A1 | 3/2008 | Milliman et al. |
| 2009/0212088 A1 | 8/2009 | Okada et al. |
| 2009/0230170 A1 | 9/2009 | Milliman |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |
| 2009/0236398 A1 | 9/2009 | Cole et al. |
| 2009/0236400 A1 | 9/2009 | Cole et al. |
| 2009/0236401 A1 | 9/2009 | Cole et al. |
| 2009/0242612 A1 | 10/2009 | Adams et al. |
| 2009/0250502 A1 | 10/2009 | Milliman |
| 2009/0255976 A1 | 10/2009 | Marczyk et al. |
| 2009/0302089 A1 | 12/2009 | Harari et al. |
| 2009/0321496 A1 | 12/2009 | Holsten et al. |
| 2010/0001036 A1 | 1/2010 | Marczyk et al. |
| 2010/0001037 A1 | 1/2010 | Racenet et al. |
| 2010/0019016 A1 | 1/2010 | Edoga et al. |
| 2010/0025452 A1 | 2/2010 | Whitman |
| 2010/0038401 A1 | 2/2010 | Milliman et al. |
| 2010/0051668 A1 | 3/2010 | Milliman et al. |
| 2010/0059571 A1 | 3/2010 | Chen et al. |
| 2010/0065607 A1 | 3/2010 | Orban, III et al. |
| 2010/0065609 A1 | 3/2010 | Schwemberger |
| 2010/0084453 A1 | 4/2010 | Hu |

FOREIGN PATENT DOCUMENTS

| | | |
|---|---|---|
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| EP | 0594436 | 10/1993 |
| EP | 1354560 | 10/2003 |
| EP | 2184018 | 5/2010 |
| FR | 2443239 | 12/1979 |
| GB | 1185292 | 3/1970 |
| GB | 2016991 | 9/1979 |
| GB | 2070499 | 9/1981 |
| SU | 1509052 | 1/1988 |
| WO | 8706448 | 11/1987 |
| WO | 8900406 | 1/1989 |
| WO | 9006085 | 6/1990 |
| WO | 0154594 | 8/2001 |
| WO | 2004032766 | 4/2004 |
| WO | 2008107918 | 9/2008 |

* cited by examiner

SURGICAL STAPLER

CROSS-REFERENCE TO RELATED APPLICATIONS

This application is a continuation of U.S. patent application Ser. No. 12/819,408, filed on Jun. 21, 2010 now U.S. Pat. No. 8,267,301, which claims priority to, and the benefit of U.S. Provisional Patent Application Ser. No. 61/235,131, filed Aug. 19, 2009, the entire contents of each of these prior applications are incorporated herein by reference.

BACKGROUND

1. Technical Field

The present disclosure relates generally to a surgical stapling device for applying surgical staples to body tissue. More particularly, the present disclosure relates to a surgical stapling device suitable for performing circular anastomosis and/or treatment to internal walls of hollow tissue organs.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 7,303,106; 6,053,390; 5,588,579; 5,119,983; 5,005,749; 4,646,745; 4,576,167; and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component as these components are approximated. The clamped tissue is stapled by driving one or more staples from the staple holding component through the staple slots so that the ends of the staples pass through the tissue and are deformed by anvil pockets of the anvil head. An annular knife is concurrently advanced to core tissue with the hollow organ to free a tubular passage within the organ.

Besides anastomosis of hollow organs, surgical stapling devices for performing circular anastomosis have been used to treat internal hemorrhoids in the rectum. Hemorrhoids are masses of tissue in the anus containing enlarged blood vessels. Internal hemorrhoids are inside the anal canal; external hemorrhoids lie outside the anal canal. In hemorrhoidectomy, the hemorrhoids are removed. Stapled hemorrhoidopexy is a surgical procedure in which the stapling device is used to remove tissue just above the hemorrhoids in order to pull the hemorrhoids back up inside the rectum and reduce the symptoms. The staples interrupt the blood flow of the superior hemorrhoidal arterial branches, cutting off the blood supply to the tissue, thus causing the hemorrhoids to shrink.

During the use of a circular stapling device for hemorrhoid treatment, the anvil head and the staple holding component of the device are inserted through and into the rectum with the anvil head and the stapling holding component in an open or unapproximated position. Thereafter, a purse string suture is used to pull the internal hemorrhoidal tissue and/or mucosal tissue toward the anvil rod. Next, the anvil head and the staple holding component are approximated to clamp the hemorrhoidal tissue and/or mucosal tissue between the anvil head and the staple holding component. The stapling device is fired to remove the hemorrhoidal tissue and/or mucosal tissue and staple the cut tissue.

It would be advantageous to provide additional structure for aligning the staple slots and the anvil pockets when the staple holding component and anvil assembly are approximated.

SUMMARY

The present invention provides in one aspect a surgical stapler comprising a handle assembly, an elongated body portion extending distally from the handle assembly, and a head portion disposed adjacent a distal portion of the elongated body portion and including an anvil assembly and a shell assembly. The anvil assembly is movable in relation to the shell assembly between spaced and approximated positions. The shell assembly includes a pusher movable distally to advance staples from the shell assembly into contact with the anvil assembly. First and second alignment pins operatively associated with the pusher have distal ends positioned distally of the pusher. The alignment pins are movable between a first non-engaged position spaced from the anvil assembly and a second position in engagement with the anvil assembly.

Preferably, the anvil assembly includes an anvil head having a first opening to receive the first alignment pin and a second opening to receive the second alignment pin. Preferably, the first and second alignment pins are frictionally received in the first and second openings, respectively. The anvil assembly can include an anvil shaft extending proximally of the anvil head and being removably mounted to an anvil retainer of the stapler.

In a preferred embodiment, advancement of the staple pusher advances the alignment pins to the second position as the first and second alignment pins are advanced through openings in the staple guide. The surgical stapler can include a plurality of staples arranged in an annular row with the alignment pins positioned radially inwardly of the annular row of staples. The alignment pins can also be positioned radially outwardly of a knife of the stapler.

In some embodiments, the anvil head has a number of openings exceeding the number of alignment pins for selective engagement of the alignment pins with the respective number of openings.

BRIEF DESCRIPTION OF THE DRAWINGS

Various embodiments of the presently disclosed device are described herein with reference to the drawings, wherein.

DETAILED DESCRIPTION OF EMBODIMENTS

The presently disclosed surgical stapler will now be described in detail with reference to the drawings in which like reference numerals designate identical or corresponding elements in each of the several views. Throughout this description, the term "proximal" will refer to the portion of the stapler closer to the operator and the term "distal" will refer to the portion of the instrument further from the operator. The presently disclosed stapler is particularly suited for surgical procedures for the treatment of colon prolapse and hemorrhoids.

Figure 1:
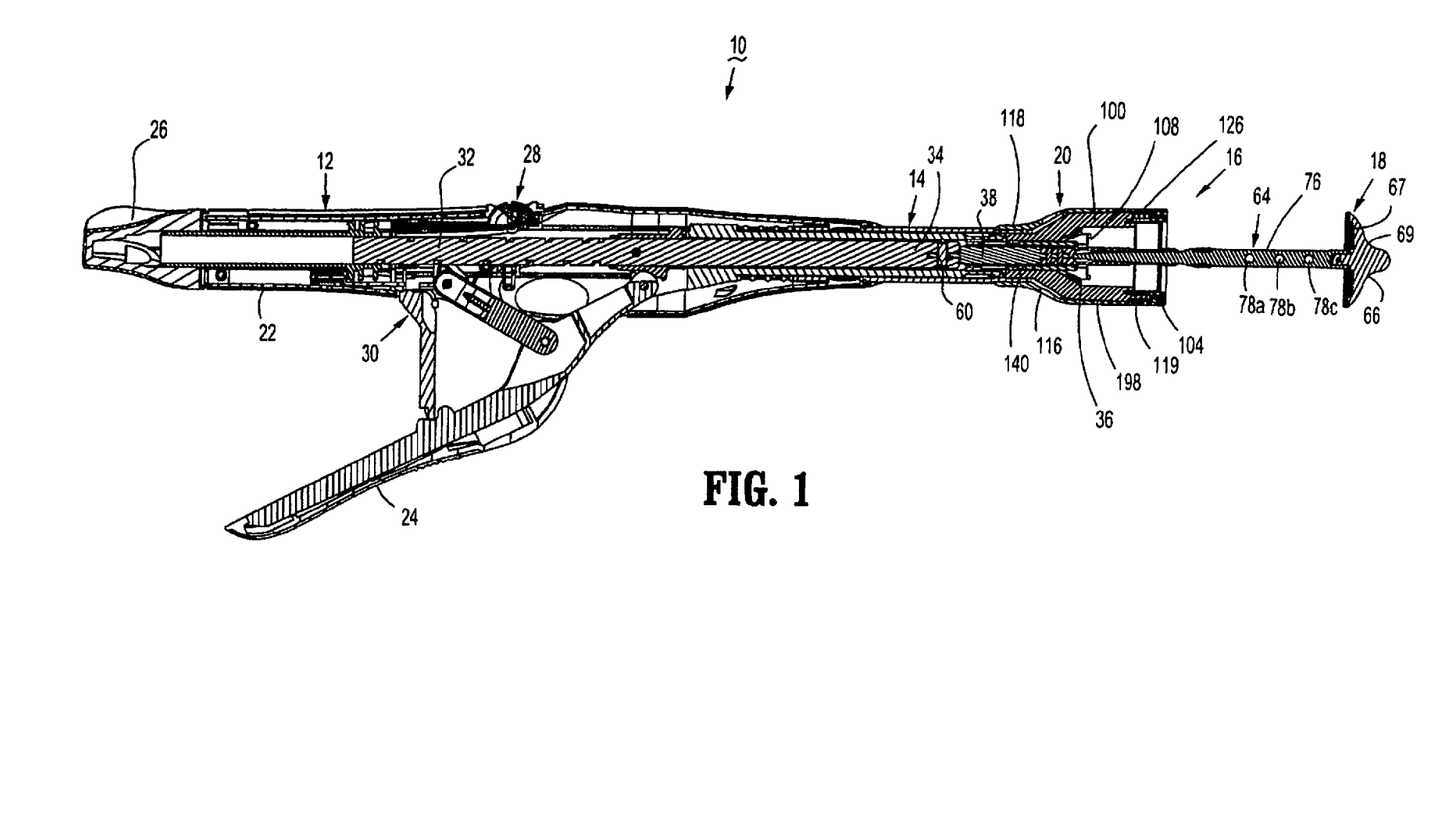
FIG. 1 is a side view of the stapler of the present disclosure incorporating the alignment pins of the present disclosure.

FIG. 1 illustrates the presently disclosed hemorrhoid stapler 10. Briefly, surgical stapler 10 includes a handle assembly 12, a central body portion 14, and a distal head portion 16. Head portion 16 includes an anvil assembly 18 and a shell assembly 20.

Handle assembly 12 includes a stationary handle 22, a firing trigger 24, an approximation knob 26, an indicator assembly 28, and a lockout mechanism 30. Approximation knob 26 functions to retract and advance a drive screw 32 to advance or retract anvil assembly 18 in relation to shell assembly 20. Firing trigger 24 functions to advance a pusher link 34 to eject staples from shell assembly 20. Each of the components of handle assembly 12 identified above are as described in U.S. Pat. No. 7,303,106 ("'106 patent"), the entire contents of which are incorporated herein by reference. Accordingly, these components and assemblies will not be described in detail herein.

Figure 2:
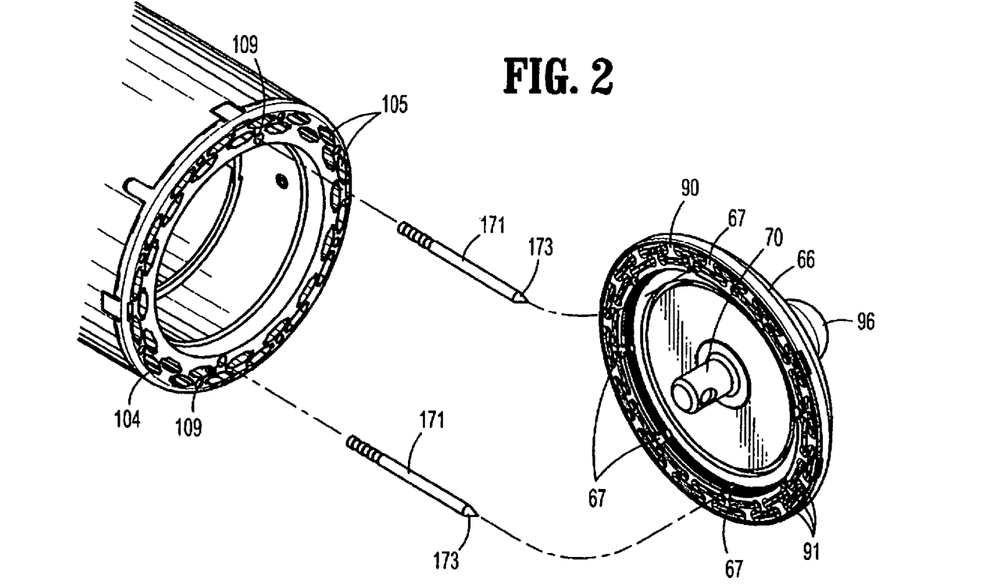
FIG. 2 is an exploded view showing the anvil head, alignment pins and an end portion of the shell assembly of FIG. 1.
Figure 2A:
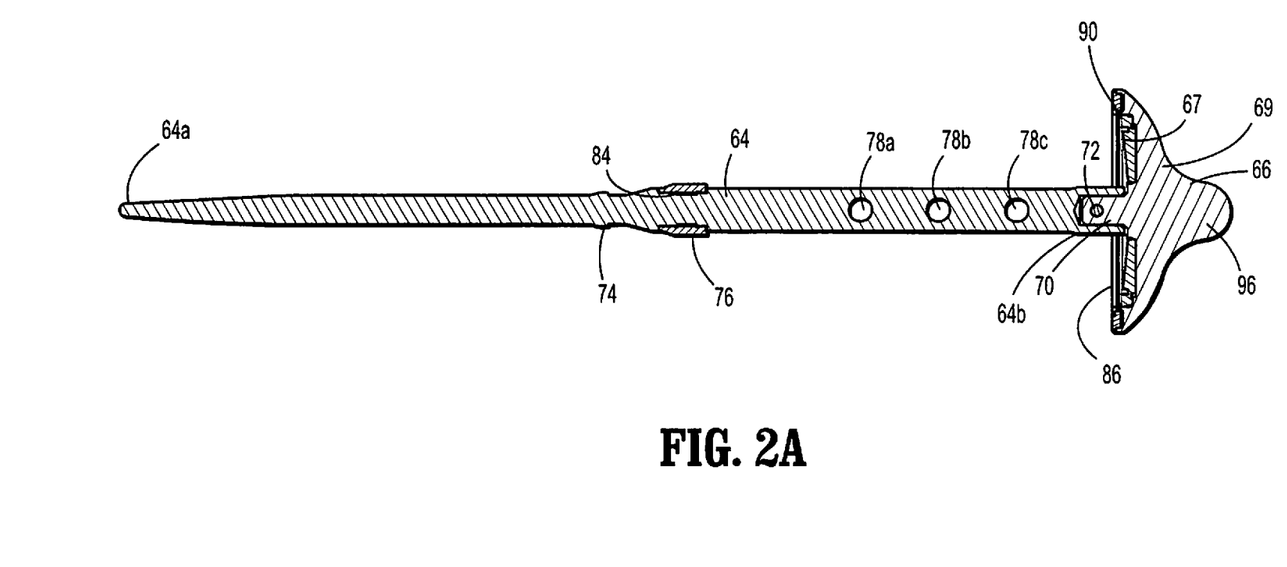
FIG. 2A is a side view of the anvil assembly of FIG. 1.

Referring to FIG. 2A, anvil assembly 18 includes an anvil shaft 64 and an anvil head 66. (The anvil shaft has been removed from FIGS. 2, 4 and 5 for clarity.) Anvil shaft or center rod 64 includes a tapered blunt end 64a. End portion 64b is dimensioned to receive a central hub portion 70 of anvil head 66. End 64b of shaft 64 and hub portion 70 of anvil head 66 each define a throughbore dimensioned to receive a pin, screw, rivet, or the like 72 for fixedly securing anvil head 66 to anvil shaft 64. The anvil head can be fixedly (non-rotatably) mounted to the anvil shaft or alternatively the anvil head can be mounted for tilted movement with respect to the anvil shaft as described for example in U.S. Pat. Nos. 6,053,390; 6,957,758; 7,168,604; 7,431,191; and U.S. Publication No. 2008-0230581. The entire contents of each of these patents/applications are incorporated herein by reference.

Figure 1A:
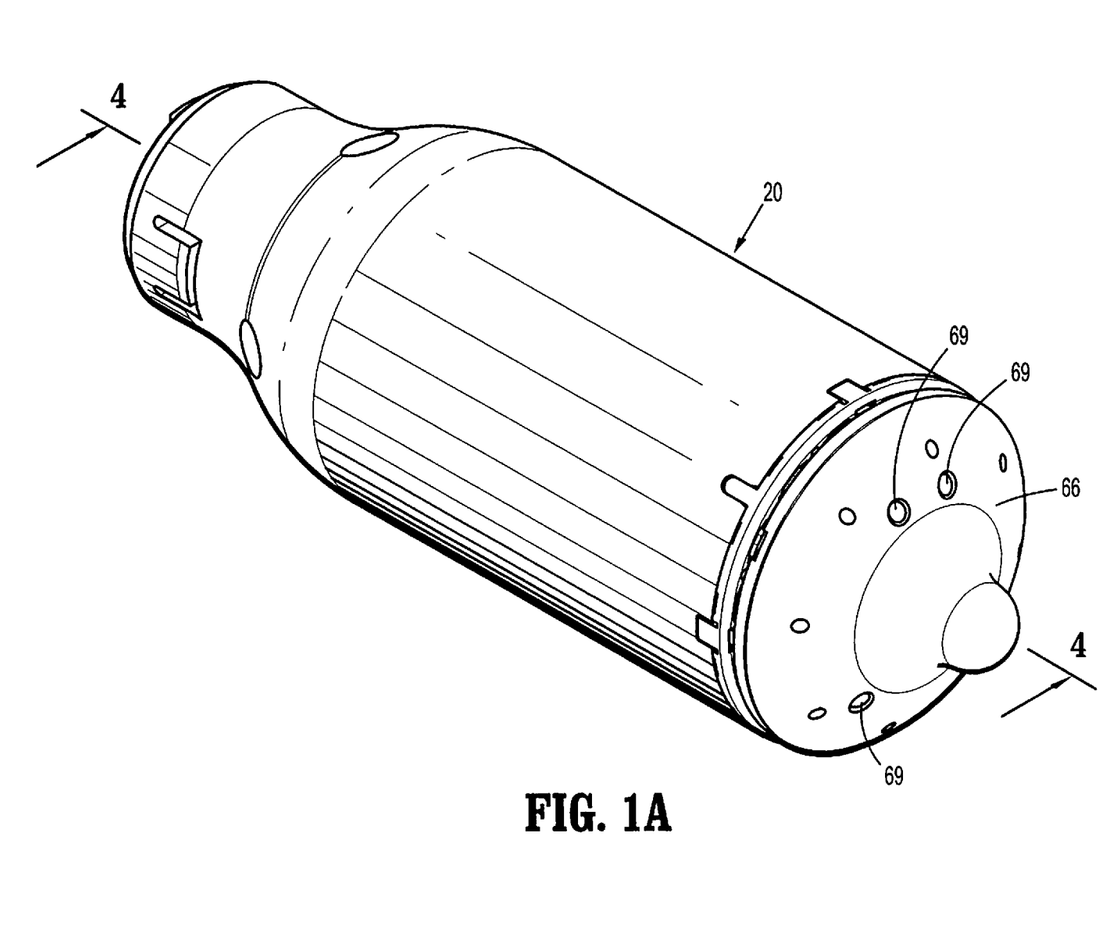
FIG. 1A is a close up perspective view of the shell assembly of the stapler of FIG. 1 with the anvil assembly in the approximated position.

Anvil shaft 64 includes a stepped surface or ring 74 between end 64a and end 64b which is configured to engage retention surfaces of flexible arms of anvil retainer 36 to releasably secure anvil shaft 64 to anvil retainer 36. Anvil retainer 36 has a bore to receive the anvil shaft 64. Anvil shaft 64 also includes over-molded splines 76. Alternatively, the splines can be machined onto the anvil shaft. The splines 76 align the anvil shaft 64 with respect to the anvil retainer 36 of the instrument to thereby align anvil assembly 18 with shell assembly 20 to ensure the staples are properly aligned with the anvil pockets. A series of longitudinally spaced suture holes 78a, 78b, 78c are formed at a distal region of the anvil shaft 64. Each of the suture holes 78 provides for a purse-string attachment location. As shown, three holes are provided, although a fewer or greater number of holes are also contemplated. The holes are configured to receive a purse-string suture therethrough. The series of holes 78 enables the user to decide the amount of tissue desired for purse stringing, e.g. hole 78a would enable additional tissue to be taken and presented for stapling. That is, holes 78 are longitudinally spaced along anvil shaft 64 such that the amount of tissue drawn into the shell assembly 20 can be controlled by properly selecting the hole 78 to which the purse string suture is inserted. Vent holes 69 of anvil head 66 are illustrated in FIG. 1A. The anvil head 66 also includes openings 67 for receipt of alignment pins discussed in detail below.

An orientation groove or grooves 84 (FIG. 2A) is provided in anvil shaft 64 beneath splines 76. Orientation groove(s) 84 functions to effect proper alignment of splines 76 about shaft 64 to facilitate proper alignment of anvil assembly 18 and shell assembly 20 when anvil assembly 18 is retracted towards shell assembly 20.

Anvil head 66 defines an outer annular recess which supports an anvil plate 90 and an inner annular recess which supports a cut ring 94. Anvil plate 90 has a plurality of anvil pockets 91 arranged in an annular array for deforming the staples are. Cutting ring 94 is an annular member that is positioned within an inner annular recess 95 formed in anvil head 66. The cutting ring 94 includes respective proximal and distal ends 98A, 98B (FIG. 5), and defines an inner proximally facing annular shoulder 98C, as well as an outer proximally facing annular surface 98D. The inner annular shoulder 98C and the annular surface 98D of the cutting ring 94 are configured and dimensioned for engagement with the anvil head 66 such that the cutting ring is retained within the recess 95. Anvil head 66 includes an inner wall with an outwardly extending finger 71A that is configured and dimensioned for engagement with the inner annular shoulder 98C, and an outer wall with an inwardly extending finger (not shown) that is configured and dimensioned for engagement with the outer annular surface 98D. During use of the stapling device 10, upon firing, the cutting ring 94 is penetrated by the annular knife 102. Anvil head 66 has a bulbous, smoothly contoured member 96 defining its distal face. Bulbous member 96 facilitates insertion of anvil head 66 through a purse-string suture.

Figure 2B:
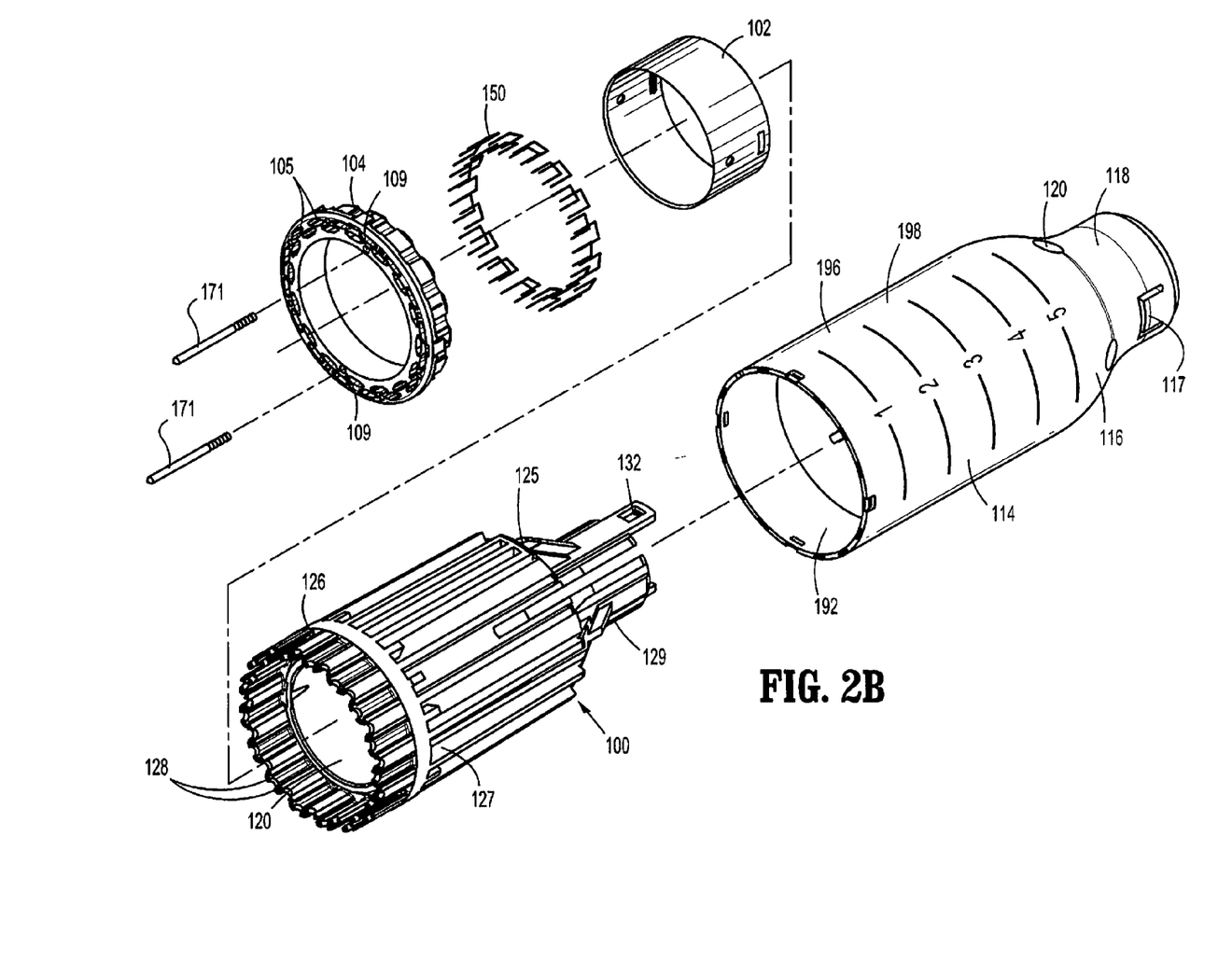
FIG. 2B is an exploded view of the shell assembly of FIG. 1.
Figure 3:
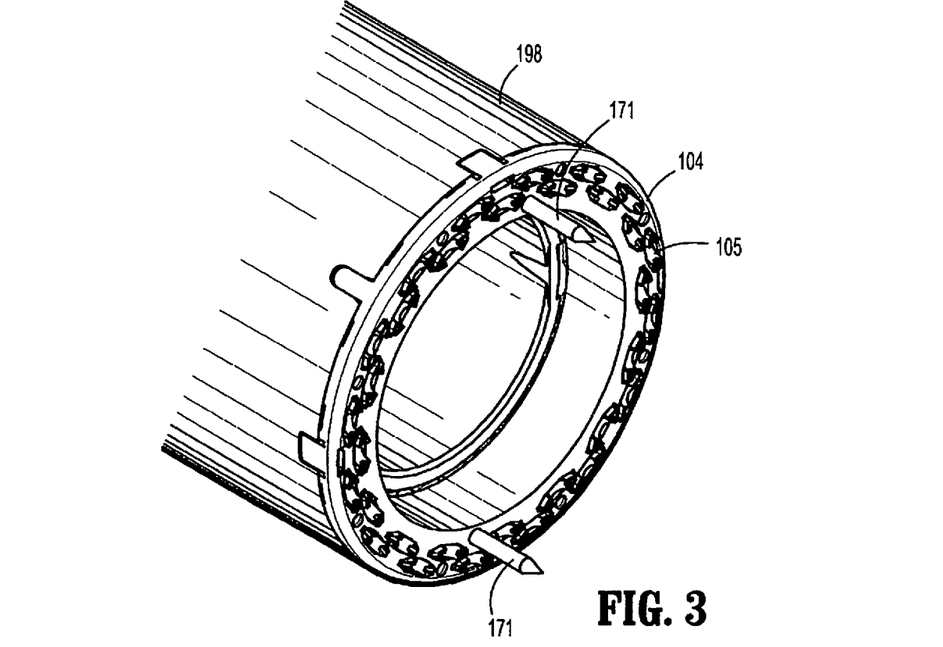
FIG. 3 is an enlarged perspective view of the end portion of the shell assembly with alignment pins.
Figure 4:
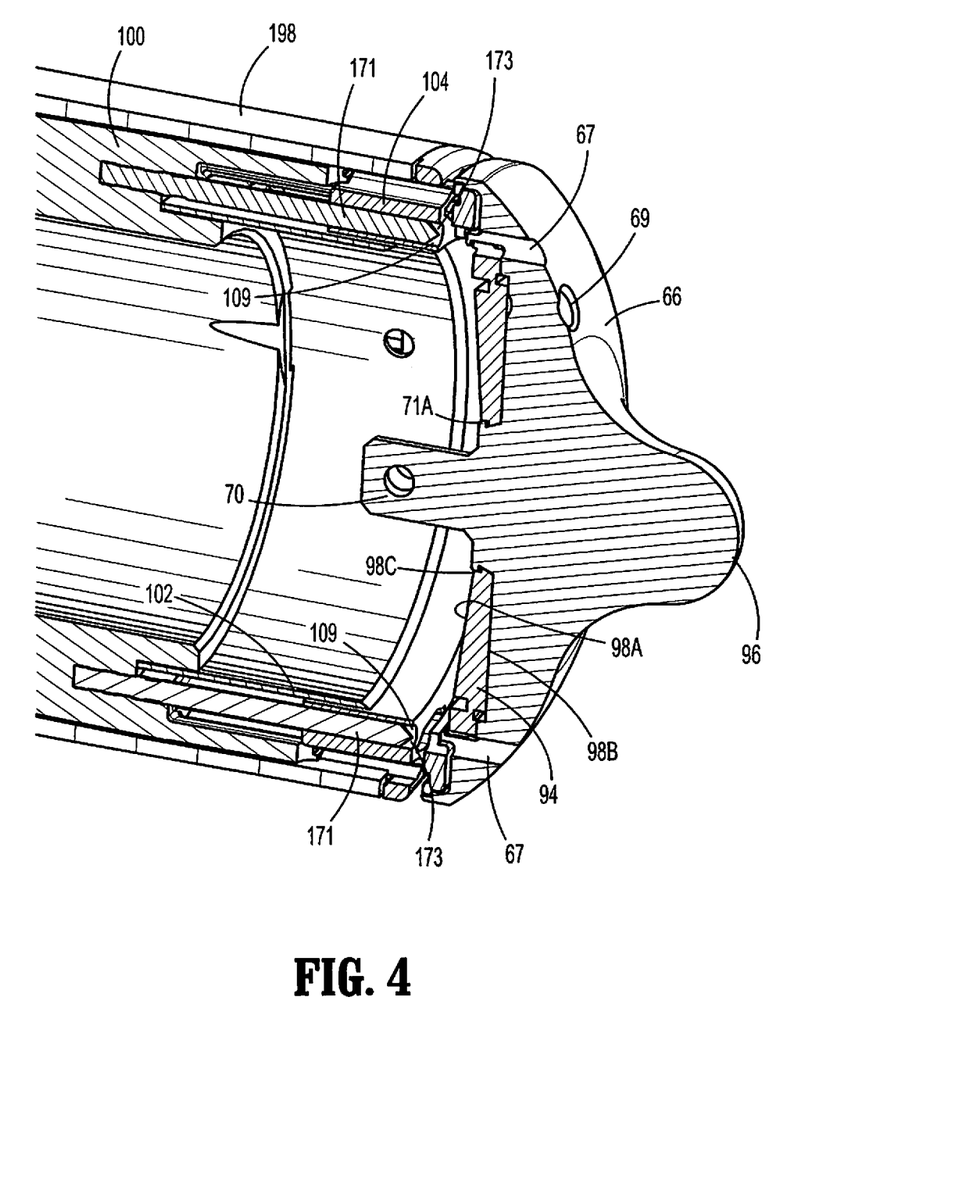
FIG. 4 is a cross-sectional view taken along lines 4-4 of FIG. 1A showing the stapler in the approximated unfired position.
Figure 5:
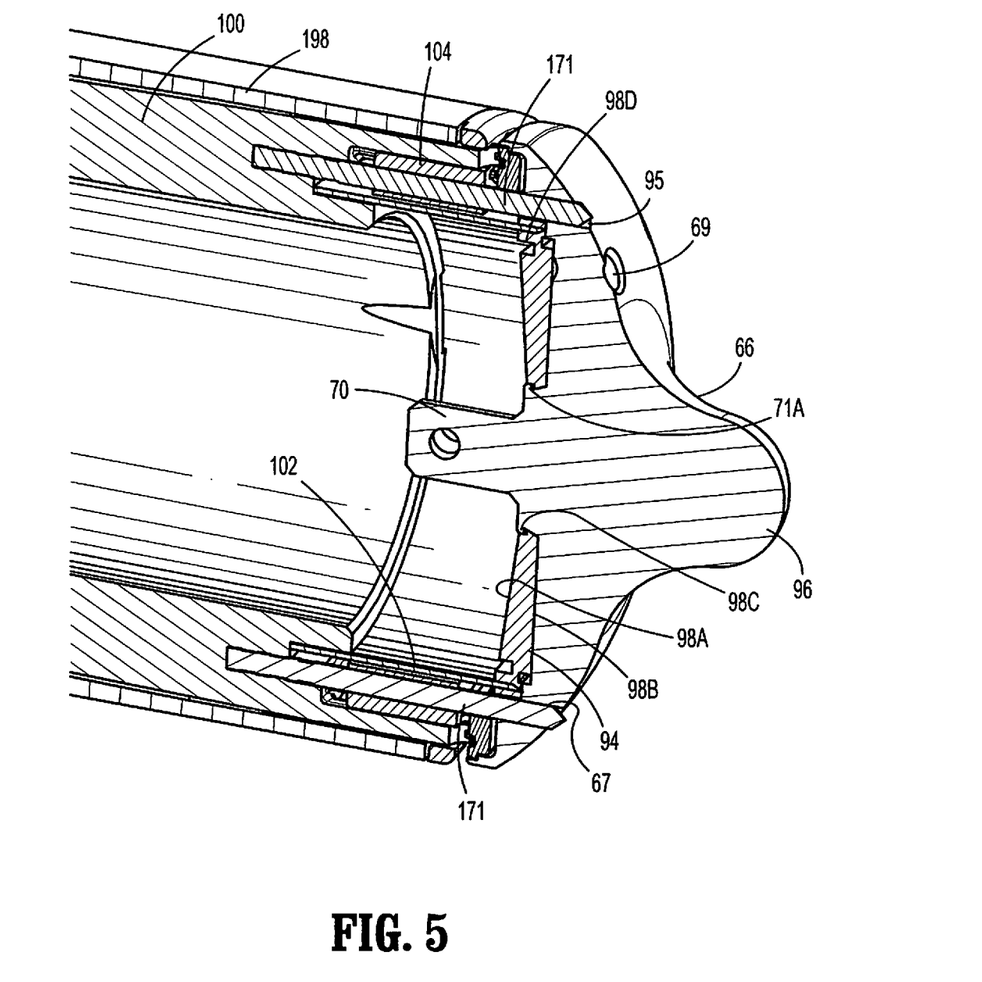
FIG. 5 is a cross-sectional view similar to FIG. 4 showing the end portion of the stapler in the fired position.

Referring to FIGS. 1, 2B and 4, shell assembly 20 is secured to the distal end of central body portion 14 in a manner substantially similar to that described in the '106 patent incorporated herein by reference. Shell assembly 20 includes a shell or housing 198, a pusher back 100 positioned within housing 198, a cylindrical knife 102, and a staple guide 104. Staple guide 104 houses one or more annular rows of staples 150.

Shell 198 includes an outer housing portion 196 and an inner guide portion 108 having grooves for mating with splines 76 on the anvil shaft 64. Outer housing portion 196 defines a throughbore 192 having a distal cylindrical section 114, a central conical section 116, and a proximal smaller diameter cylindrical section 118. A plurality of openings 120 are formed in conical section 116, dimensioned to permit fluid and tissue passage during operation of stapler 10. A pair of diametrically opposed flexible engagement members 117 are formed on proximal cylindrical section 118 of shell 198 for reception in openings formed on a distal end body portion 14 to secure shell 198 to body portion 14.

Pusher back 100 includes a central throughbore 120 which is slidably positioned about inner guide portion 108 of shell 98. Pusher back 100 includes a distal cylindrical section 127 which is slidably positioned within distal cylindrical section 114 of shell 198, a central conical section 125, and a proximal smaller diameter cylindrical section 129. The proximal end of pusher back 100 includes members 132 which are configured to lockingly engage with pusher link 34 of stapler 10 as described in the '106 patent incorporated by reference herein. Pusher back 100 also defines a receptacle for receiving excised tissue.

Referring to FIG. 1, a rigid bushing 140 is supported in the proximal end of inner guide portion 108 of shell 198. Bushing 140 defines a throughbore dimensioned to slidably receive anvil retainer 36 and anvil shaft 64 of anvil assembly 18.

The distal end of pusher back 100 includes a pusher 126 (FIG. 2B). Pusher 126 includes a multiplicity of distally extending fingers 128 dimensioned to be slidably received within slots 105 formed in staple guide 104 to eject staples 150 therefrom. Cylindrical knife 102 is retained within the central throughbore 120 of pusher back 100 to fixedly secure knife 102 in relation to pusher 126. Knife 102 may be retained within pusher back 100 using adhesives, crimping, pins, friction, etc. The distal end of knife 102 includes a circular cutting edge.

The rigid bushing 140 is supported in the proximal end of inner guide portion 108 of shell 198. Bushing 140 defines a throughbore dimensioned to slidably receive anvil retainer 36 and anvil shaft 64 of anvil assembly 18. Anvil retainer 36 is connected to drive screw 32 by connector 38 as a proximal end of connector 38 is connected to a distal end of drive screw 32 via pin 60. Bushing 140 provides lateral support for flexible arms 48 of anvil retainer 36 when the anvil assembly 18 has been approximated to prevent disengagement of anvil assembly 18 from anvil retainer 36. In the unapproximated position, flexible arms 48 of anvil shaft 64 are positioned externally of bushing 140 to permit removal of anvil assembly 18 from anvil retainer 36.

As discussed above, stapler 10 is particularly suitable for use in surgical procedures for treating hemorrhoids. During such a procedure, an access port can be inserted into the anus to facilitate access to the hemorrhoids. Next, a purse string suture (not shown) is placed into, above or in the vicinity of the hemorrhoids and the anvil assembly 18 is inserted through the access port into the anus and rectum. Bulbous member 96 of anvil head 66 functions to allow smooth passage of anvil assembly 18 past the purse string suture. Anvil assembly 18 and shell assembly 20 are approximated via knob 26 to draw the hemorrhoids into shell assembly 20.

When surgical stapler 10 is fully approximated (FIGS. 1A and 4), firing trigger 24 can be actuated or fired in a manner described in the '106 patent 10 to staple, sever and allow removal of a portion of the hemorrhoids. Thereafter, stapler 10 is removed from the body with the excised tissue contained within the receptacle of pusher back 100 within shell assembly 20.

Shell assembly 20 has a plurality of projections shown in the form of alignment pins 171 engagable with alignment openings 67 in the anvil assembly (see e.g. FIGS. 2 and 4). More specifically, the pins 171 extend distally from pusher back 100 and extend through openings 109 in the staple guide 104, functioning as described below to help align the anvil head 66 and shell assembly 20 and to limit axial movement of the anvil head 66, especially in the instance where a relatively long anvil shaft is provided such as in certain hemorrhoid staplers. The alignment pins 171 can be attached to the pusher back 100 via interference ribs press fit into holes into pusher back 100 or by other methods such as screw threads. It should be appreciated that the alignment pins (projections) can also be utilized on other circular staplers in addition to stapler 10. The pins 171 can have tapered ends 173 as shown. Alternately, they can have planar ends or other configurations.

The pins function to limit movement of the anvil head 166 with respect to the shell assembly 120. In one embodiment, the pins 171 have an outer dimension substantially equal to the inner diameter of the alignment openings 67 of the anvil assembly to frictionally fit within the alignment openings 67 with sufficient force for retention, while not inhibiting re-approximation of the anvil assembly. In other embodiments, the pins can have a smaller outer dimension in relation to the inner diameter of the alignment openings to thereby more loosely be seated in the alignment openings, while still functioning to limit axial movement and rotational movement of the anvil head. The pins 171 are preferably outboard (radially outward) of the circular knife 102 of the stapler 10 and inboard (radially inward) of the staples 150. Pins 171 are shown spaced approximately 180 degrees apart. Two or more pins substantially equally radially spaced or spaced at varying intervals can be provided. Although the pins 171 are shown for use with an anvil shaft having through holes 175 for a purse string suture, the pins can be used with staplers having other anvil shafts. Also, the alignment pins 171 can be used with non-pivoting anvils as well as pivotally mounted anvils which move from non-tilted to tilted operative positions, such as those disclosed in the U.S. patents/publication listed above.

The anvil head 66 is shown with a plurality of openings 67 to receive alignment pins 171. The openings are positioned radially inward of the annular array of staple forming (anvil) pockets. At minimum, the number of anvil openings 67 is equal to the number of alignment pins 171. However, it is also contemplated, as shown in the illustrated embodiment, that there are more anvil openings 67 than alignment pins. For example, in the illustrated embodiment, two alignment pins 171 are provided while eight anvil openings 67 are provided. In this manner, the alignment pins 171 can align with two of the respective anvil openings 67 at various orientations of the anvil head 66 with respect to the shell assembly 20.

In use, upon firing of the stapler 10, the pusher back 100 is advanced distally to advance the staple pusher 126 with fingers 128 into contact with the staples 150 positioned within slots 105 in the staple guide 104. As the pusher 126 is advanced distally, alignment pins 171, operatively associated with the pusher 126 via their attachment thereto, are likewise moved distally. The alignment pins 171 move distally from a retracted, non-engaged position shown in FIG. 4 where they are retracted within the shell assembly to an advanced position protruding beyond the shall assembly and into engagement with the anvil openings 67 of the anvil head 66.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical stapler comprising:
   a handle portion;
   an elongated shaft extending from the handle portion; and
   an end effector disposed at a distal end of the elongated shaft, the end effector including,
      a shell assembly including a pusher block and a first alignment pin operatively coupled to the pusher block and extending distally therefrom, the first alignment pin being longitudinally fixed relative to the pusher block; and
      an anvil selectively repositionable with respect to the shell assembly between spaced and approximated positions,
   wherein the pusher block is translatable such that the first alignment pin is repositionable between a first position spaced from the anvil and a second position in engagement with the anvil.

2. The surgical stapler of claim 1, wherein the anvil includes an opening for receiving the first alignment pin.

3. The surgical stapler of claim 2, wherein the first alignment pin frictionally engages the opening.

4. The surgical stapler of claim 3, wherein engagement of the first alignment pin and the anvil limits axial movement of the anvil with respect to the shell assembly.

5. The surgical stapler of claim 2, further including:
a second alignment pin operatively coupled to the pusher block, and
a second opening in the anvil for receiving the second alignment pin.

6. The surgical stapler of claim 1, wherein the anvil includes an anvil head and an anvil shaft extending proximally from the anvil head, the anvil shaft being removably mounted to an anvil retainer of the stapler.

7. The surgical stapler of claim 1, wherein advancement of the pusher block advances the first alignment pin from the first position to the second position.

8. The surgical stapler of claim 1, further including:
an annular array of staples disposed in the shell assembly and operatively associated with the pusher block, and
an annular array of pockets located on the anvil for deforming the staples.

9. The surgical stapler of claim 8, wherein the shell assembly includes an annular knife and the first alignment pin is positioned radially outwardly of the annular knife.

10. The surgical stapler of claim 8, wherein the first alignment pin is positioned radially inwardly of the annular array of staples.

11. The surgical stapler of claim 10, wherein the anvil includes an anvil head having a first opening dimensioned to receive the first alignment pin, the first opening being positioned radially inwardly of the annular array of pockets.

12. A surgical stapling apparatus comprising:
a handle;
a shaft having first and second ends, the first end coupled to the handle;
an end effector coupled to the second end of the shaft, the end effector including,
a shell assembly with a pusher block, the pusher block having a first protrusion extending distally therefrom, the first protrusion being longitudinally fixed relative to the pusher block; and
an anvil repositionable with respect to the shell assembly between spaced and approximated positions,
wherein the pusher block is repositionable with respect to the anvil such that the first protrusion is moved between a first position that is spaced from the anvil and a second position that is in engagement with the anvil.

13. The surgical stapling apparatus of claim 12, further including a second protrusion extending distally from the pusher block.

14. The surgical stapling apparatus of claim 13, wherein the anvil includes an anvil head, the anvil head having a first opening for receiving the first protrusion and a second opening for receiving the second protrusion.

15. The surgical stapling apparatus of claim 13, wherein the anvil includes an anvil shaft extending proximally from the anvil head, the anvil shaft being removably mounted to an anvil retainer of the stapler.

16. The surgical stapling apparatus of claim 12, wherein the anvil includes an anvil head, the anvil head including a first opening for receiving the first protrusion.

17. The surgical stapler of claim 16, wherein engagement of the first protrusion and the anvil limits axial movement of the anvil with respect to the shell assembly.

18. The surgical stapler of claim 12, further including:
an annular array of staples disposed in the shell assembly and operatively associated with the pusher block, and
an annular array of pockets located on the anvil for deforming the staples.

* * * * *